United States Patent
Da Silva et al.

(10) Patent No.: US 10,045,734 B2
(45) Date of Patent: Aug. 14, 2018

(54) FLUID REPLACEMENT DEVICE

(75) Inventors: J. Ricardo Da Silva, Ann Arbor, MI (US); Wieslaw Gronek, Northbridge, MA (US); Andrew V. Halpert, Brookline, MA (US); Robert I. Rudko, Holliston, MA (US); Mark Tauscher, Medfield, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 459 days.

(21) Appl. No.: 12/657,144

(22) Filed: Jan. 14, 2010

(65) Prior Publication Data
US 2010/0274217 A1 Oct. 28, 2010

Related U.S. Application Data

(60) Provisional application No. 61/206,254, filed on Jan. 28, 2009.

(51) Int. Cl.
*A61B 5/00* (2006.01)
*A61B 5/20* (2006.01)
(Continued)

(52) U.S. Cl.
CPC .............. *A61B 5/4839* (2013.01); *A61B 5/20* (2013.01); *A61M 5/1723* (2013.01);
(Continued)

(58) Field of Classification Search
CPC .... A61M 5/168; A61M 5/172; A61M 5/1723; A61M 2202/0496; A61B 5/20; A61B 5/4839; A61B 19/56; G06F 19/3468
(Continued)

(56) References Cited

U.S. PATENT DOCUMENTS

| 3,954,010 A | 5/1976 | Hilblom |
| 4,132,644 A | 1/1979 | Kolberg |

(Continued)

FOREIGN PATENT DOCUMENTS

| EP | 0258690 | 3/1988 |
| JP | 2008/110150 | 5/2008 |

(Continued)

OTHER PUBLICATIONS

Urexact® 2000 System, mhtml:file//C:\Documents%20and%20Settings/bob/Local%20Settings\Temporary%20Intt . . . (Jul. 22, 2005) (three (3) pages).

(Continued)

*Primary Examiner* — Kami A Bosworth
(74) *Attorney, Agent, or Firm* — Nixon & Vanderhye P.C.

(57) ABSTRACT

A console includes a weighing subsystem responsive to a first fluid source and a urine collection chamber. A pump infuses fluid from the first fluid source into a patient. A processing subsystem is responsive to the weighing subsystem. Based on the weight of the first fluid source and of the urine collection chamber, urine output and amount of fluid infused into the patient from the first fluid source are determined. A user can set a desired fluid balance and the amount of at least one additional fluid delivered. An actual fluid balance is calculated based on the determined urine output, the determined amount of fluid infused from the first fluid source, and the set amount of the additional fluid delivered. The pump is controlled based on actual fluid balance and set desired fluid balance so actual fluid balance becomes the same or approximately the same as the desired fluid balance.

10 Claims, 10 Drawing Sheets

(51) Int. Cl.
*A61M 5/172* (2006.01)
*G06F 19/00* (2018.01)
*A61B 34/00* (2016.01)

(52) U.S. Cl.
CPC .......... *G06F 19/3468* (2013.01); *A61B 34/25* (2016.02); *A61M 2202/0496* (2013.01)

(58) Field of Classification Search
USPC ................ 604/29–31, 65–67, 503, 890.1
See application file for complete search history.

(56) References Cited

U.S. PATENT DOCUMENTS

| | | | |
|---|---|---|---|
| 4,146,029 A | 3/1979 | Ellinwood, Jr. | |
| 4,204,957 A | 5/1980 | Weickhardt | |
| 4,216,462 A | 8/1980 | McGrath et al. | |
| 4,229,299 A | 10/1980 | Savitz et al. | |
| 4,261,360 A | 4/1981 | Perez | |
| 4,275,726 A | 6/1981 | Schael | |
| 4,291,692 A | 9/1981 | Bowman et al. | |
| 4,343,316 A | 8/1982 | Jespersen | |
| 4,448,207 A | 5/1984 | Parrish | |
| 4,449,538 A | 5/1984 | Corbitt et al. | |
| 4,504,263 A | 3/1985 | Steuer et al. | |
| 4,658,834 A | 4/1987 | Blankenship et al. | |
| 4,712,567 A | 12/1987 | Gille et al. | |
| 4,728,433 A | 3/1988 | Buck et al. | |
| 4,813,925 A | 3/1989 | Anderson, Jr. et al. | |
| 4,923,598 A | 5/1990 | Schal | |
| 4,994,026 A | 2/1991 | Fecondini | |
| 5,098,379 A | 3/1992 | Conway et al. | |
| 5,176,148 A | 1/1993 | Weist et al. | |
| 5,207,642 A | 5/1993 | Orkin et al. | |
| 5,573,506 A | 11/1996 | Vasko | |
| 5,722,947 A | 3/1998 | Jeppsson et al. | |
| 5,769,087 A | 6/1998 | Westphal et al. | |
| 5,814,009 A | 9/1998 | Wheatman | |
| 5,891,051 A | 4/1999 | Han et al. | |
| 5,910,252 A | 6/1999 | Truitt et al. | |
| 5,916,153 A | 6/1999 | Rhea, Jr. | |
| 5,916,195 A | 6/1999 | Eshel et al. | |
| 5,981,051 A | 11/1999 | Motegi et al. | |
| 6,010,454 A | 1/2000 | Arieff et al. | |
| 6,171,253 B1 | 1/2001 | Bullister et al. | |
| 6,231,551 B1 | 5/2001 | Barbut | |
| 6,272,930 B1 | 8/2001 | Crozafon et al. | |
| 6,514,226 B1 | 2/2003 | Levin et al. | |
| 6,531,551 B2 | 3/2003 | Levin et al. | |
| 6,537,244 B2 | 3/2003 | Paukovits et al. | |
| 6,554,791 B1 | 4/2003 | Cartledge et al. | |
| 6,640,649 B1 | 11/2003 | Paz et al. | |
| 6,740,072 B2 | 5/2004 | Starkweather | |
| 6,752,779 B2 | 6/2004 | Paukovits et al. | |
| 6,796,960 B2 | 9/2004 | Cioanta et al. | |
| 6,827,702 B2 | 12/2004 | Lebel et al. | |
| 6,942,637 B2 | 9/2005 | Cartledge et al. | |
| 7,029,456 B2 | 4/2006 | Ware et al. | |
| 7,044,002 B2 | 5/2006 | Ericson et al. | |
| 7,137,964 B2 | 11/2006 | Flaherty | |
| 7,278,983 B2 | 10/2007 | Ireland et al. | |
| 7,727,222 B2 | 6/2010 | Da Silva et al. | |
| 7,736,354 B2 | 6/2010 | Gelfand et al. | |
| 7,758,562 B2 | 7/2010 | Gelfand et al. | |
| 7,758,563 B2 | 7/2010 | Gelfand et al. | |
| 7,837,667 B2 | 11/2010 | Gelfand et al. | |
| 8,075,513 B2 | 12/2011 | Rudko et al. | |
| 8,444,623 B2 | 5/2013 | Gelfand et al. | |
| 2002/0025597 A1 | 2/2002 | Matsuda | |
| 2002/0072647 A1 | 6/2002 | Schock et al. | |
| 2002/0107536 A1 | 8/2002 | Hussein | |
| 2002/0151834 A1 | 10/2002 | Utterberg | |
| 2002/0161314 A1 | 10/2002 | Sarajarvi | |
| 2003/0048185 A1 | 3/2003 | Citrebaum et al. | |
| 2003/0048432 A1 | 3/2003 | Jeng et al. | |
| 2003/0114786 A1 | 6/2003 | Hiller et al. | |
| 2004/0025597 A1 | 2/2004 | Ericson et al. | |
| 2004/0059295 A1 | 3/2004 | Cartledge et al. | |
| 2004/0081585 A1 | 4/2004 | Reid | |
| 2004/0087894 A1 | 5/2004 | Flaherty | |
| 2004/0122353 A1 | 6/2004 | Shahmirian et al. | |
| 2004/0133187 A1 | 7/2004 | Hickle | |
| 2004/0163655 A1 | 8/2004 | Gelfand et al. | |
| 2004/0167415 A1 | 8/2004 | Gelfand et al. | |
| 2004/0167464 A1 | 8/2004 | Ireland et al. | |
| 2004/0176703 A1 | 9/2004 | Christensen | |
| 2004/0193328 A1 | 9/2004 | Zaitsu et al. | |
| 2004/0243075 A1 | 12/2004 | Harvie | |
| 2005/0027254 A1 | 2/2005 | Vasko | |
| 2005/0065464 A1 | 3/2005 | Talbot et al. | |
| 2005/0085760 A1 | 4/2005 | Ware et al. | |
| 2006/0052764 A1 | 3/2006 | Gelfand et al. | |
| 2006/0064053 A1 | 3/2006 | Bollish et al. | |
| 2006/0184084 A1 | 8/2006 | Ware | |
| 2006/0235353 A1 | 10/2006 | Gelfand et al. | |
| 2006/0253064 A1 | 11/2006 | Gelfand et al. | |
| 2006/0270971 A1 | 11/2006 | Gelfand et al. | |
| 2007/0088333 A1 | 4/2007 | Levin et al. | |
| 2008/0027409 A1 | 1/2008 | Rudko et al. | |
| 2008/0033394 A1 | 2/2008 | Gelfand et al. | |
| 2008/0171966 A1 | 7/2008 | Rudko et al. | |
| 2008/0221512 A1 | 9/2008 | DaSilva | |
| 2010/0234797 A1 | 9/2010 | Gelfand et al. | |
| 2010/0280443 A1 | 11/2010 | Gelfand et al. | |
| 2010/0280444 A1 | 11/2010 | Gelfand et al. | |
| 2010/0280445 A1 | 11/2010 | Gelfand et al. | |
| 2011/0046516 A1 | 2/2011 | Paz et al. | |
| 2012/0259308 A1 | 10/2012 | Gelfand et al. | |

FOREIGN PATENT DOCUMENTS

| | | |
|---|---|---|
| WO | WO 96/16685 | 6/1996 |
| WO | WO 96/28209 | 9/1996 |
| WO | WO 97/16220 | 5/1997 |
| WO | WO 99/06087 A1 | 2/1999 |
| WO | WO 1999/06087 A1 | 2/1999 |
| WO | WO 2006/041496 A1 | 4/2006 |

OTHER PUBLICATIONS

Bard Lubricath 3-Way Catheters, Bard Medical Division, http://www/bardmedical.com/urology/cathtour/3way.html (Jul. 6, 2005) (one (1) page).

Foley Catheter Introduction, Foley Catheter, http://www/wmedicineheatlth.com/articles/11633-1.asp; http://www.emedicinehealth.com/articles/11633-8.asp (Jul. 6, 2005) (two (2) pages).

Gambro Acute Renal Failure, Prisma, http://www.gambro.com/Page.asp?id=2446; http://www.gambro.com/upload/press_media_toolkit/download_images/Prisma.jpg (Jul. 6, 2005) (two (2) pages).

Angiometrx, The Metricath System, http://www.angiometrx.com/Metricath%20System.htm (Jul. 6, 2005) (one (1) page).

Merit Medical Systems, Inc., 2003 Annual Report; Balloon Inflation Devices & Pressure Monitoring Syringes; Transducers and Accessories, http://www.corporatewindow.com/annuals/mmsi03/10kpages5.html (Jul. 6, 2005) (three (3) pages).

Millar Instruments: Single Sensor Cardiology Catheters, Cardiovascular Mikro-Tip Pressure Transducer Catheters, http://www.millarinstruments.com/products/cardio/cardio_sngldual.html (Jul. 6, 2005) (five (5) pages).

Infusion Dynamics: Power Infuser, The Power Infuser, http://www.infusiondynamics.com/powerinfuser/ (Apr. 4, 2005) (two (2) pages).

S215 Ultra Low Profile Single Point Load Cell—Strain Guage Sensors and Load Cells, Ultra-Low Profile Cell—S215, http://smdsensors.com/detail_pgs/s215.htm (Apr. 4, 2005) (two (2) pages).

Rihal et al., Incidence and Prognostic Importance of Acute Renal Failure After Percutaneous Coronary Intervention, Circulation, May 14, 2002, pp. 2259-2264 (six (6) pages).

(56) References Cited

OTHER PUBLICATIONS

Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21 (eleven (11) pages).
Wakelkamp et al., The influence of drug input rate on the development of tolerance to frusemide, Br. J. Clin. Pharmacol 1998, 46:479-487, pp. 479-487 (nine (9) pages).
Stevens, Melissa A., MD et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb., 1999, pp. 403-411 (nine (9) pages).
Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5 (four (4) pages.
Gloor, James M. and Vincente E. Torres, Reflux and Obstructive Nephropathy, Atlas of Diseases of the Kidney, on-line edition, vol. Two, Section I, Ch. 8, pp. 8.1-8.25 (date unknown) (twenty-five (25) pages).
Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415 (three (3) pages).
Lelarge et al., Acute Unilateral Renal Failure and Contralateral Ureteral Obstruction, American Journal of Kidney Diseases, vol. XX, No. 3, Sep. 1992, pp. 286-288 (three (3) pages).
Doty et al., Effect of Increased Renal Venous Pressure on Renal Function, The Journal of Trauma: Injury, Infection and Critical Care, vol. 47, No. 6, Dec. 1999, pp. 1000-1003 (four (4) pages).
Edelson et al., Pharmacokinetics of Iohexol, a New Nonionic Radiocontrast Agent, in Humans, Journal of Pharmaceutical Sciences, vol. 73, No. 7, Jul. 1984, pp. 993-995 (three (3) pages).
Hvistendahl et al., Renal Hemodynamic Response to Gradated Ureter Obstruction in the Pig, Nephron 1996, 74:168-74 (seven (7) pages).
Pederson et al., Renal Water and Sodium Handling During Gradated Unilateral Ureter Obstruction, Scand J. Urol Nephrol, 2002, 36:163-72 (ten (10) pages).
Brezis et al., Hypoxia of the Renal Medulla—Its Implications for Disease, New England Journal of Medicine, vol. 322, No. 10, Mar. 9, 1995, pp. 647-655 (nine (9) pages).
Heyman et al., Pathophysiology of Radiocontrast Nephropathy: A Role for Medullary Hypoxia, Investigative Radiology, vol. 34, No. 11, Nov. 1999, pp. 685-691 (seven (7) pages).
Office Action of the Canadian Intellectual Property Office for Canadian Patent Application No. 2,579,829 dated Jun. 13, 2008 (two (2) pages).
Written Opinion of the International Searching Authority for PCT Application No. PCT/US05/08948 dated Oct. 3, 2006 (five (5) pages).
Written Opinion of the International Searching Authority for PCT Application No. PCT/US2007/009683 dated Nov. 24, 2008 (eight (8) pages).
Written Opinion of the International Searching Authority for PCT Application No. PCT/US07/09685 dated Jul. 18, 2008 (twelve (12) pages).
Written Opinion of the International Searching Authority for PCT Application No. PCT/US07/09684 dated Jul. 21, 2008 (nine (9) pages).
Written Opinion of the International Searching Authority for PCT Application No. PCT/US08/07845 dated Sep. 17, 2008 (seven (7) pages).
Written Opinion of the International Searching Authority for PCT Application No. PCT/US08/07841 dated Sep. 18, 2008 (six (6) pages).
Written Opinion of the International Searching Authority for PCT Application No. PCT/US09/02739 dated Jun. 19, 2009 (six (6) pages).
Written Opinion of the International Searching Authority for PCT Application No. PCT/US2007/021791 dated May 8, 2008 (nine (9) pages).
Written Opinion of the International Searching Authority for PCT Application No. PCT/US 10/00137 dated Mar. 16, 2010 (eleven (11) pages).
Levin et al, High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, p. 153 (one (1) page).
Mawer et al., "Value of Forced Diuresis in Acute Barbiturate Poisoning", Jun. 29, 1968, British Medical Journal, 2, 790-793.
Bart et al., "Ultrafiltration in Decompensated Heart Failure With Cardiorenal Syndrome", The New England Journal of Medicine, Dec. 13, 2012, pp. 2296-2304, Massachusetts Medical Society.
Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, pp. 1-10.
Dorval et al., "Feasibility Study of the RenalGuard™ Balanced Hydration System: A Novel Strategy for the Prevention of Contrast-Induced Nephropathy in High Risk Patients", International Journal of Cardiology, 2011, pp. 1-5, Elsevier Ireland Ltd.
Felker et al., "Diuretic Strategies in Patients With Acute Decompensated Heart Failure", The New England Journal of Medicine, Mar. 3, 2011, vol. 364, No. 9, pp. 797-805.
Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, pp. e21-e181 and Correction sheet e424.
Marenzi et al., "Prevention of Contrast Nephropathy by Furosemide With matched Hydration". The MYTHOS (Induced Diuresis With Matched Hydration Compared to Standard Hydration for Contrast Induced Nephropathy Prevention) Trial, JACC: Cardiovascular Interventions, vol. 5, No. 1, 2012 The American College of Cardiology Foundation, pp. 90-97.
Mawer et al., "Value of Forced Diuresis in Acute Barbiturate Poisoning", British Medical Journal, Jun. 29, 1968, 2, pp. 790-793.
Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, pp. 1997-2003.
Stevenson et al., "Editorial Comment, Torrent or Torment From the Tubules?", Challenge of the Cardiorenal Connections, Journal of the American College of Cardiology, vol. 45, No. 12, 2005, pp. 2004-2007.
Written Opinion of the International Searching Authority dated Jun. 12, 2015 for International Application No. PCT/US2015/020196, 5 pages.

FLUID REPLACEMENT DEVICE

RELATED APPLICATIONS

This application hereby claims the benefit of and priority to U.S. Provisional Application Ser. No. 61/206,254, filed on Jan. 28, 2009 under 35 U.S.C. §§ 119, 120, 363, 365, and 37 C.F.R. § 1.55 and § 1.78.

FIELD OF THE INVENTION

The subject invention relates to fluid management systems.

BACKGROUND OF THE INVENTION

Systems have been proposed to automatically measure the fluid delivered to a patient and fluids expelled or taken from a patient.

U.S. Pat. No. 4,291,692, for example, discloses and IV drop counter, a urine drop counter, and a microcomputer controlling an infusion pump. U.S. Pat. No. 7,029,456 discloses a "networked" system with no less than four separate units. See also U.S. Pat. No. 4,994,026 disclosing separate load scales and a control unit primarily used for dialysis.

In a cath lab, for example, a patient has a contrast agent injected into his veins, the patient's vessels are imaged, and a therapy is administered, e.g., a stent or the like is inserted into the patient. After this procedure, the contrast agent will collect in the patient's kidneys. The toxic nature of these contrast agents are well documented as is contrast nephropathy. See corresponding application Ser. No. 10/936,945 published as Published Patent Application No. 2006/0052764 incorporated herein by this reference.

Also, during cardiac surgery, the patient may be administered a fair amount of fluid. After surgery, a diuretic may be administered and the nurse instructed to allow the patient to expel urine at a rate greater than fluid administered to the patient (e.g., drugs, nutritional supplements, saline, sodium bicarbonate, and the like). Managing this prescribed fluid balance can be difficult and time consuming.

BRIEF SUMMARY OF THE INVENTION

Accordingly, it is desirable to hydrate the patient sufficiently to encourage the patient to urinate and expel the toxic contrast agent and also to infuse the patient with fluid to balance the urine expelled by the patient with the fluid infused into the patient so that the patient does not become dehydrated.

But, the cath lab and other surgical and recovery sites are too small and crowded to accommodate separate urine drop counters, weight scales, or "networked" units. Moreover, the attending nurses do not have the time to learn complex systems. This is perhaps why the proposed systems of the prior art have not been commercially successful.

It is therefore an object of the invention to provide a new automated fluid replacement device. In one preferred embodiment, the new fluid replacement device is self-contained. The device also automatically takes into account fluid taken by the patient from multiple sources. The device has a user friendly interface where the nurse can enter different settings and a display which provides the information the nurse needs. Once the desired settings are entered, the device operates automatically.

It is a further object of the invention, in one example, to provide a device which can automatically provide therapy, even when, for example, a patient's urine output is less than the amount of fluid infused into the patient.

A fluid replacement device in accordance with an example of the invention includes a console with a weighing subsystem responsive to a first fluid source and a urine collection chamber, and a pump configured to pump fluid from the first fluid source into a patient. A processing subsystem in the console is responsive to the weighing subsystem and is configured to determine, based on the weight of the first fluid source and the weight of the urine collection chamber, the patient's urine output and the amount of fluid infused into the patient from the first fluid source. The processing subsystem is further configured to control the pump to adjust the operation of the pump based on the patient's urine output and the amount of fluid infused into the patient. A user interface in the console allows the user to set a desired fluid balance for the patient and to set an amount of at least one additional fluid delivered to the patient. The processing subsystem is responsive to these settings and is further configured to automatically calculate the patient's actual fluid balance based on the determined urine output, the determined amount of fluid infused into the patient from the first fluid source, and the set amount of the at least one additional fluid delivered to the patient. The pump is controlled based on the actual fluid balance and the set desired fluid balance until the actual fluid balance is the same as or approximately the same as the desired fluid balance.

The typical user interface includes a display and the processing subsystem may be configured to display the actual fluid balance, the set desired fluid balance, the determined urine output, the determined amount of fluid infused into the patient, and the set amount of the at least one additional fluid delivered to the patient.

The processing subsystem may further be configured to automatically detect when the determined urine output is less than a set fluid balance. In response, the processing subsystem controls the pump to infuse a minimum preset amount of fluid from the source of fluid. The processing subsystem can also automatically detect when the determined urine output is greater than the total of the determined amount of fluid infused into the patient and the set amount of the at least one additional fluid delivered to the patient and, in response, it controls the pump to infuse fluid from the first source of fluid until the actual fluid balance equals or approximates the set desired fluid balance.

In one version, there are means for setting an amount of at least one additional fluid expelled by the patient. The processing subsystem is responsive to this setting and is configured to calculate an actual fluid balance based on the determined urine output, the determined amount of fluid infused into the patient from the first fluid source, the set amount of the at least on additional fluid delivered to the patient, and the set amount of the at least one additional fluid expelled by the patient.

There may also be means for setting a bolus amount of fluid to be injected into the patient from the first fluid source. Then, the processing subsystem is further configured to be responsive to the set bolus amount and to control the pump until the actual fluid balance is the same as or approximately the same as the set bolus amount.

One novel fluid replacement device comprises a console including a pump infusing fluid from a first fluid source into a patient, and a processing subsystem configured to determine the patient's urine output and the amount of fluid infused into the patient from the first fluid source. The processing subsystem is also configured to control the pump to adjust the operation of the pump based on the patient's urine output and the amount of fluid infused into the patient. A user interface in the console allows the user to set a desired fluid balance for the patient and set an amount of at least one additional fluid delivered to the patient. The processing subsystem is responsive to these setting and automatically calculates the actual fluid balance based on the determined urine output, the determined amount of fluid infused into the patient from the first fluid source, and the set amount of the at least one additional fluid delivered to the patient. The pump is controlled based on the actual fluid balance and the set desired fluid balance until the actual fluid balance is the same as or approximately the same as the desired fluid balance.

The subject invention also features a fluid replacement method. The amount of urine expelled by a patient is determined. Fluid from a first fluid source is infused into a patient. The amount of fluid infused into the patient from the first fluid source is determined. The operation of the pump is adjusted based on the patient's urine output and the amount of fluid infused into the patient.

A desired fluid balance for the patient can be set. An amount of at least one additional fluid delivered to the patient can be input. An actual fluid balance is calculated based on the determined urine output, the determined amount of fluid infused into the patient from the first fluid source, and the set amount of the at least one additional fluid delivered to the patient. The pump is controlled based on the actual fluid balance and the set desired fluid balance until the actual fluid balance is the same as or approximately the same as the desired fluid balance.

Urine expelled by the patient may be collected in a urine collection bag and determining the amount of urine expelled by the patient may including weighing the collection bag. Also, determining the amount the fluid infused into the patient from the first fluid source may include weighing the first fluid source. The actual fluid balance, the set desired fluid balance, the determined urine output, the determined amount of fluid infused into the patient, and the set amount of at least one additional fluid delivered to the patient are all quantities which are typically displayed.

The method may further include detecting when the determined urine output is less than a set fluid balance and, in response, controlling the pump to automatically infuse a minimum preset amount of fluid from the source of fluid. The method may further include detecting when the determined urine output is greater than the total of the determined amount of fluid infused into the patient and the set amount of the at least one additional fluid delivered to the patient and, in response, controlling the pump to automatically infuse fluid from the source of fluid until the actual fluid balance equals or approximates the set desired fluid balance.

The method may further include setting an amount of at least one additional fluid expelled by the patient and calculating an actual fluid balance based on the determined urine output, the determined amount of fluid infused into the patient from the first fluid source, the set amount of the at least one additional fluid delivered to the patient, and the set amount of the at least one additional fluid expelled by the patient.

The method may further include setting a bolus amount of fluid to be infused into the patient from the fluid source and automatically controlling the pump until the actual fluid balance is the same as or approximately the same as the set bolus amount.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
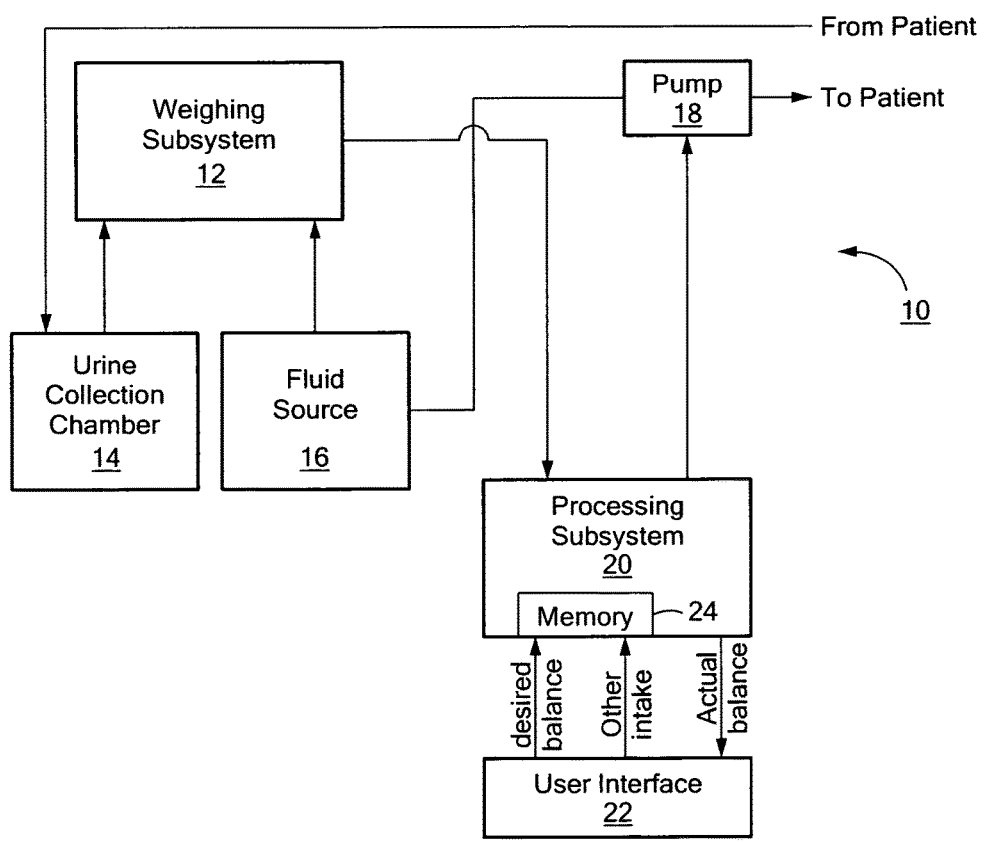
FIG. 1 is a block diagram depicting the primary components associated with an example of a fluid management system in accordance with the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Fluid replacement system 10, FIG. 1, in one example, includes weighing subsystem 12 responsive to both the weight of urine collection chamber 14 and source of fluid 16. Pump 18 is configured to pump fluid from source 16 into a patient as shown. Pump 18 is controlled by processing subsystem 20, e.g., a computer, a field programmable gate array, application specific integrated circuit, microprocessor, controller, or the like.

Processing subsystem 20 is configured to be responsive to weighing subsystem 12 and is configured (e.g., programmed) to determine, based on the weight of fluid source 16, the amount of fluid infused into the patient over some interval (e.g., an hour). Processing subsystem 20 may also monitor the operation history of pump 18 to determine the amount of fluid infused into the patient from source 16. Other means for determining the amount of fluid infused into the patient are within the scope of the subject invention. Processing subsystem 20 further determines, based on the weight of urine collection chamber 14, the patient's urine output over some interval. Other means for determining urine output are possible. The programming associated with processing subsystem 20 then typically controls pump 18 to adjust the operation of pump 18 based on the patient's urine output and the amount of fluid infused into the patient (e.g., manually or from other infusion pumps, IV drops, and the like).

There are also means for setting a desired fluid balance for a given patient and for setting an amount of at least one additional fluid delivered to the patient. Such means may include user interface 22 (e.g., a monitor and keyboard or touch screen). As shown, the set desired balance may be stored in memory 24 associated with processing subsystem 20 and a set amount of the at least one additional fluid delivered to the patient ("other intake") may also be stored in memory 24. Memory 24 can also be used to store default values for various parameters.

Processing subsystem 20 includes programming which takes these parameters as inputs and calculates an actual patient fluid balance based on the determined urine output, the determined amount of fluid infused into the patient from the first fluid source, and the set amount of the at least one additional fluid delivered to the patient by other means. Processing subsystem 20 controls pump 18 based on the actual fluid balance and the set desired fluid balance until the actual fluid balance is the same as or approximately the same as the desired fluid balance.

Figure 2:
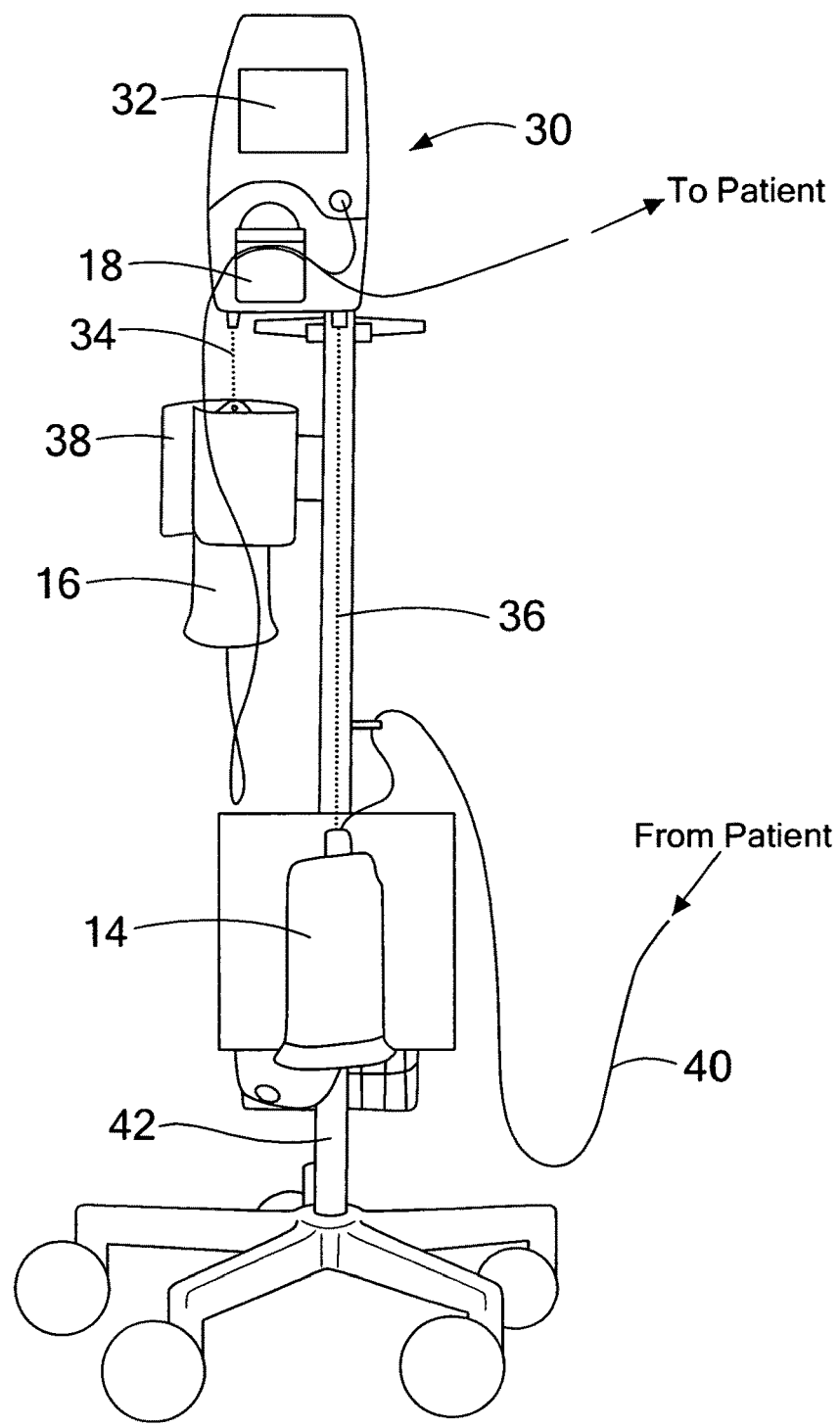
FIG. 2 is a schematic front view of a fluid management device incorporating the components depicted in FIG. 1 in an integrated manner.

FIG. 2 depicts one preferred fluid management device including integrated console 30 including weighing subsystem 12, FIG. 1, pump 18, processing subsystem 20, memory 24, and user interface 22 in the form of menu driven touch screen display 32. Chain 34 is connected on one end to the weighing subsystem inside console 30 (e.g., one or more strain gauges) and includes a hook for hanging fluid source 16 (e.g., a saline bag). Chain 36 is also connected on one end to the weighing subsystem inside console 30 and terminates in a hook for hanging urine bag 14. Tubing 38 extends from fluid source 16 through pump 18 and to a needle inserted into the vein of a patient. Tubing 40 extends from a catheter connected to the patient's urinary tract to urine collection bag 14. See Published Patent Application No. 2006/0052764 incorporated herein by this reference.

The result is a stand alone integrated device which can be coupled to N pole 42 and moved with the patient when he leaves the cath lab as opposed to multiple units wired together or "networked" units.

Figure 3:
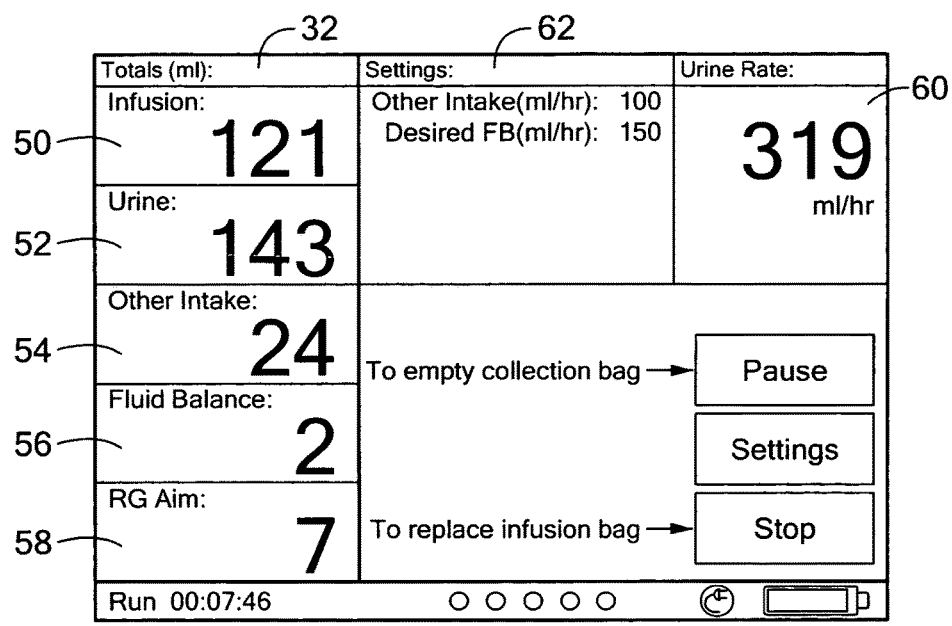
FIG. 3 is a schematic view of the display of the device shown in FIG. 2.
Figure 4:
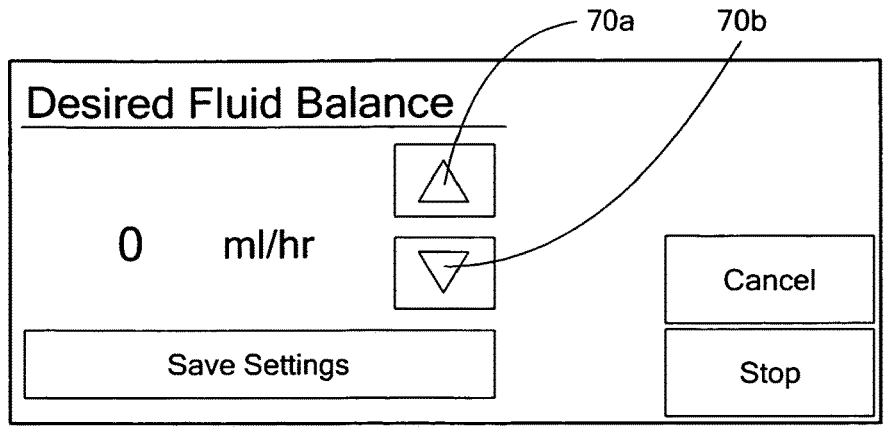
FIG. 4 is a view of the display shown in FIG. 3 configured to allow the user to set a desired fluid balance.
Figure 5:
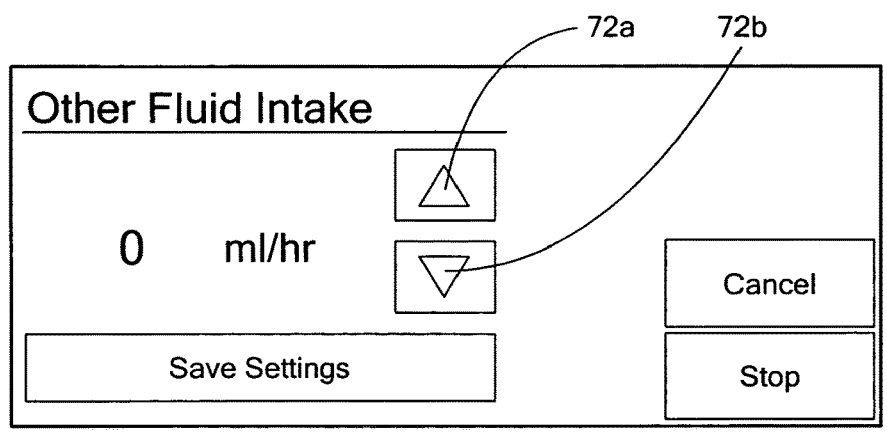
FIG. 5 is a view of the display shown in FIG. 3 configured to allow the user to set the amount of another fluid delivered to the patient.
Figure 6:
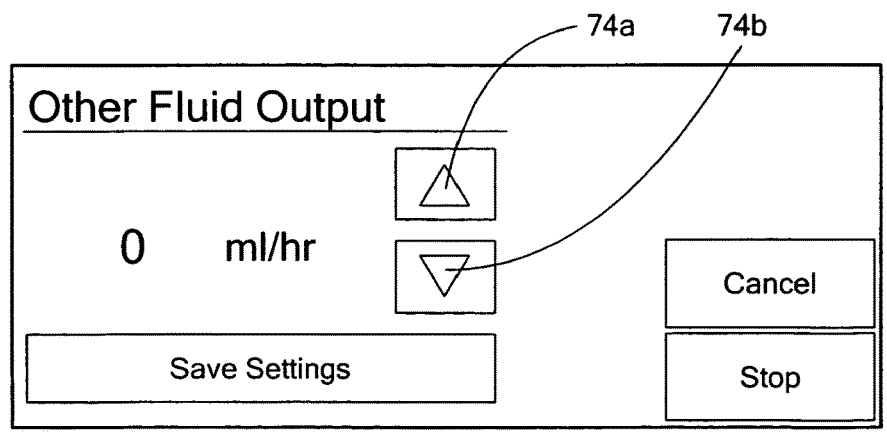
FIG. 6 is a schematic view of the display shown in FIG. 3 allowing the user to set the amount of fluid expelled by the patient other than urine.

FIG. 3 shows how the processing subsystem is configured to display, on display 32, FIG. 2, the determined infused amount at 50, FIG. 3, the determined urine output at 52, the set "other" patient fluid intake at 54, the calculated actual fluid balance at 56, and the desired fluid balance at 58. All amounts are typically in milliliters. The present urine output rate is calculated and displayed as shown in 60. Touch screen menu area 62 allows the user to input and set a desired fluid balance, the "other intake," and, in one embodiment, other fluids expelled by the patient, if known. Once set, these parameters are displayed as shown. In FIG. 4, the desired fluid balance can be set using buttons 70a and 70b. In FIG. 5, the other fluid intake can be set using buttons 72a and 72b. In FIG. 6, the other fluid output can be set using buttons 74a and 74b. All three menus are activated by selecting the "settings" area 62, FIG. 3.

Figure 7:
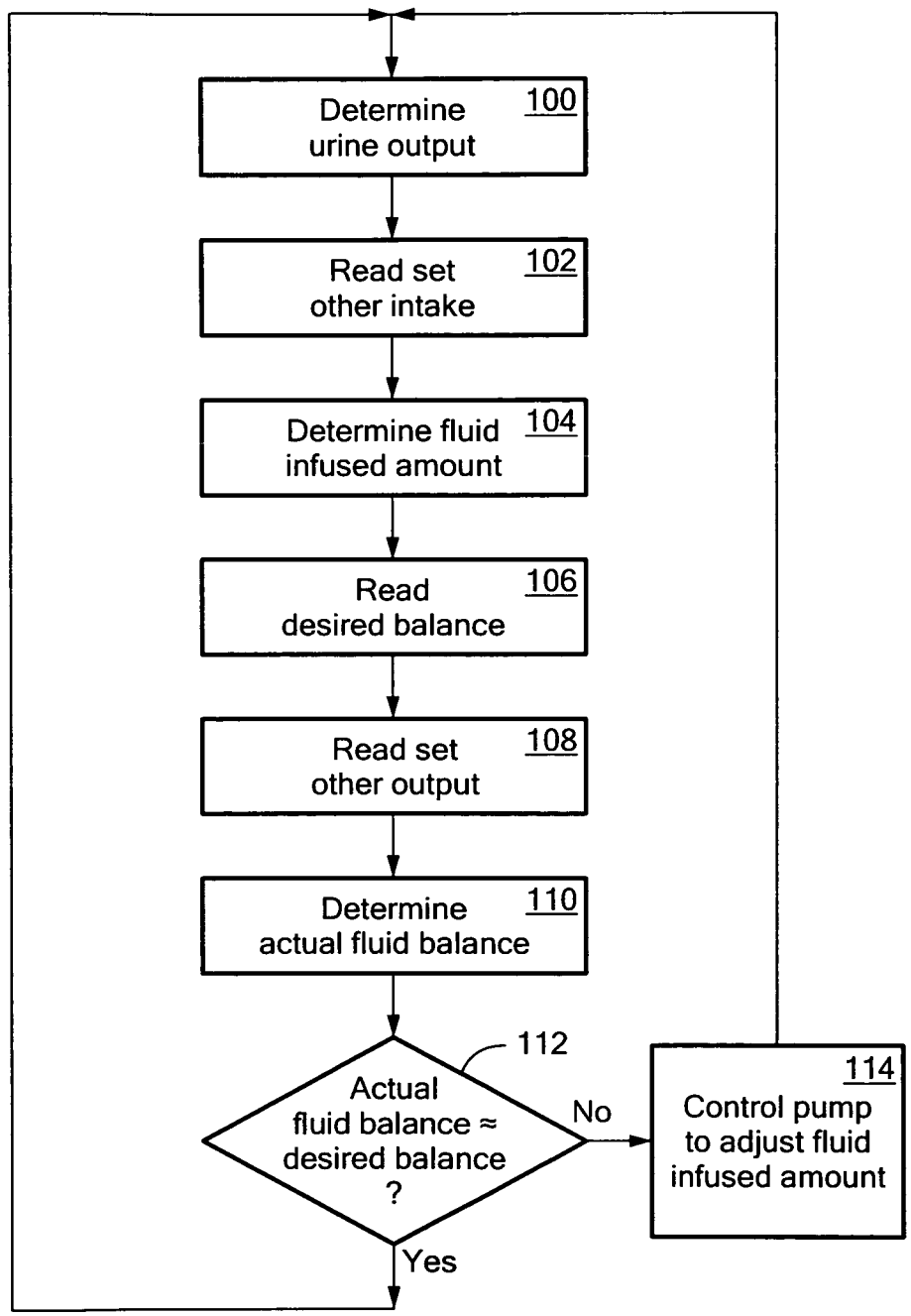
FIG. 7 is a flow chart depicting the primary steps associated with the programming of the processing subsystem shown in FIG. 1 and also depicting the primary steps associated with a fluid balancing method in accordance with the subject invention.

Processing subsystem 20, FIG. 1 is programmed as shown in FIG. 7. A patient may have a contrast agent injected to his veins, and the patient will have been imaged and subject to some form of a therapy such as the introduction of a stent. Or, the patient may be recovering from surgery and administered saline, drugs, nutritional supplements, and the like. Once the patient's urinary tract is connected to urine collection bag 14, FIG. 2 and the saline bag is connected to the patient, therapy begins at some point during the patient's stay in the cath lab or other location. At step 100, the patient's urine output is determined. The set "other intake" is read (see display area 62, FIG. 3) from memory 24, FIG. 1, step 102, FIG. 7. The fluid infused amount is determined, step 104, based on the weight of source 16, FIG. 2. The desired fluid balance is read from memory 24, FIG. 1 (see display area 62, FIG. 3), step 106, FIG. 7. If there has been a setting for fluid expelled by the patient other than collected in urine collection chamber 14, FIG. 2, that quantity is also read, step 108, FIG. 7.

Then, processing subsystem 20, FIG. 1, determines the actual fluid balance, step 110, FIG. 7 and displays it (see display area 56, FIG. 3). The actual fluid balance is the amount infused via pump 18, FIG. 1 plus the set "other intake" less the urine output collected in chamber 14, FIG. 1 and any set "other output."

In step 112, FIG. 7, the calculated actual fluid balance is compared to the set desired balance (see display area 58, FIG. 3). If the balance is perfect or within a predetermined range, no action is taken as shown at step 112 in FIG. 7. If the calculated fluid balance is less than or more than the desired set fluid balance by a predetermined amount, however, processing subsystem 20, FIG. 1 controls pump 18, step 114, FIG. 7 to inject less or more fluid from fluid source 16, FIG. 1 until the actual fluid balance equals or approximates the desired fluid balance.

Figure 8:
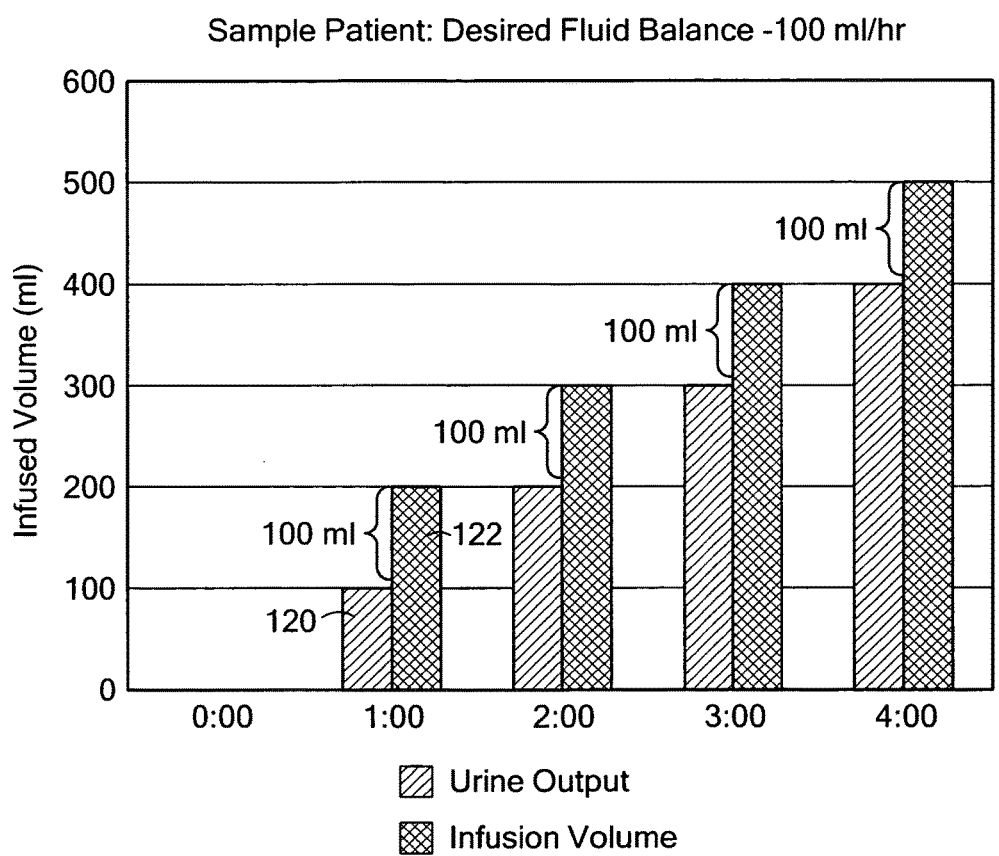
FIG. 8 is a graph showing a therapy scenario where the desired fluid balance setting is positive.

FIG. 8 shows how at the beginning of therapy, a desired fluid balance of +100 ml/hr is set, the actual urine output is determined to be 100 ml in the first hour as shown at 120. In response, processing subsystem 20, FIG. 1 controls pump 18 to infuse the patient with 200 ml of fluid from source 16 as shown at 122 in FIG. 8. This particular scenario assumes the "other intake" is set at 0. FIG. 8 also shows the determined urine output is compared to the infused amount during the second through fourth hours of therapy.

Figure 9:
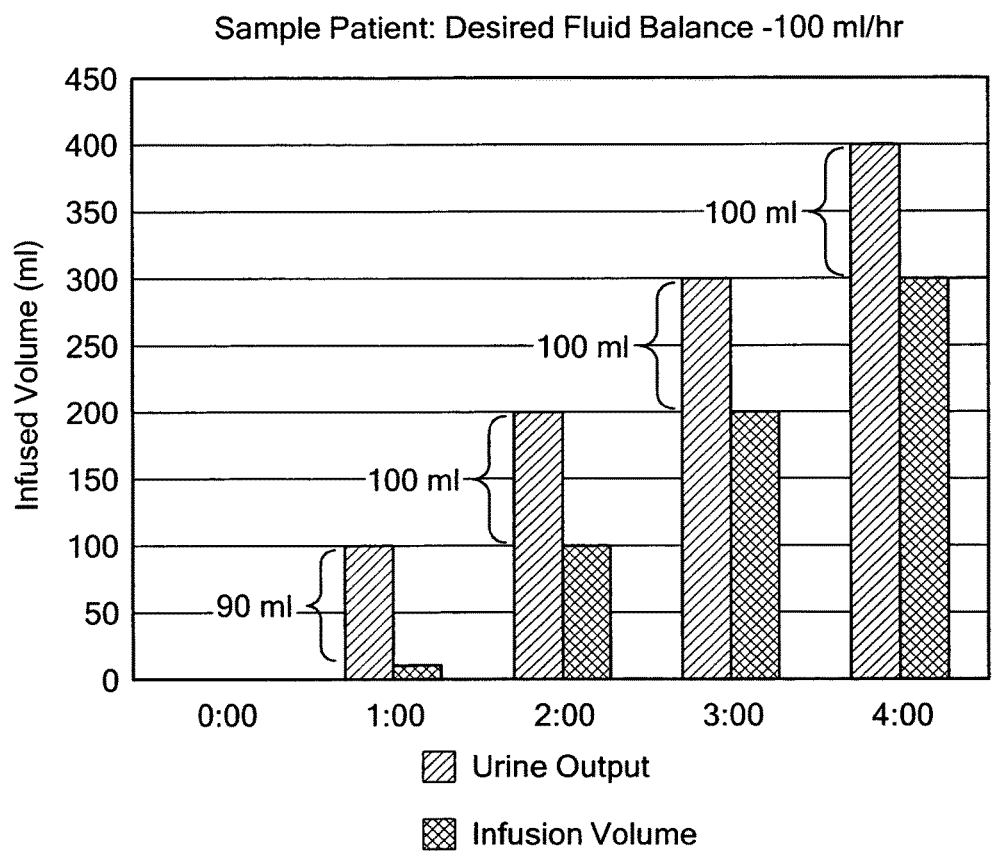
FIG. 9 is a graph showing a therapy scenario where the desired fluid balance setting is negative.
Figure 10:
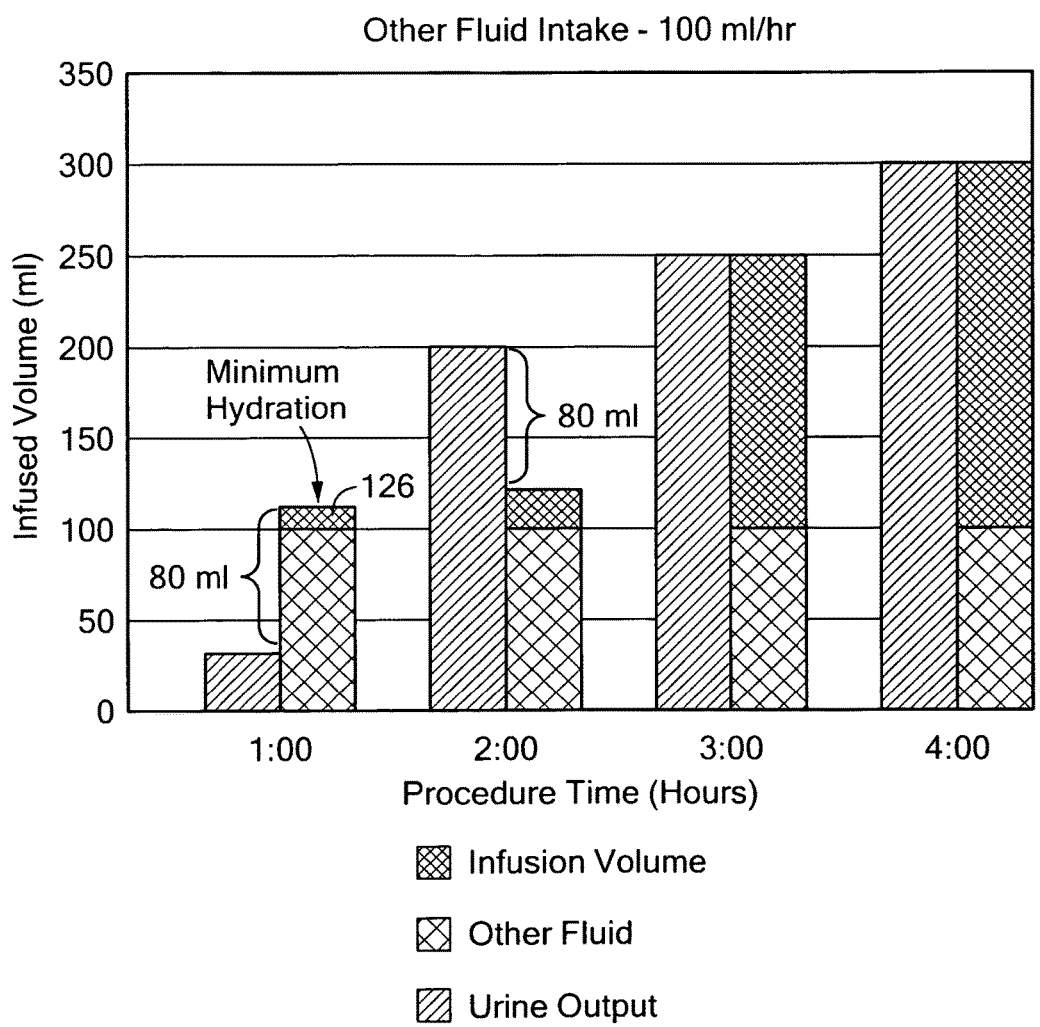
FIG. 10 is a graph showing a therapy scenario where fluid intake from another source has been set by the user.

FIG. 9 shows an example of where the desired fluid balance is negative. FIG. 10 shows a scenario where the "other intake" has been set by the nurse (see 54, FIG. 3). In the first hour, this patient has expelled only about 25 ml but has taken in about 100 ml of fluid from the "other intake" source. The desired balance is set to zero. In this case, processing subsystem 20, FIG. 1 detects that the desired urine output is less than a set fluid balance and is programmed, in response, to control pump 18, FIG. 1 to infuse a minimum preset amount of fluid from the source of fluid as shown at 126 in FIG. 10. This minimum preset amount of fluid may be 10 ml per hour, for example, a sufficient amount to keep the patient's vein open, but the default amount may be changed by the user via display 32, FIG. 2.

In the second hour, the patient's urine output is 200 ml but the amount infused is only about 25 ml and again, the set fluid received by the patient from another source is about 100 ml. Processing subsystem 20, FIG. 1, detects that the urine output is greater than the total of the determined amount of fluid infused into the patient and the set amount of the additional fluid delivered to the patient and, in response, the processing subsystem is programmed to control pump 18, FIG. 1 to infuse fluid from the source of fluid until the actual fluid balance equals or approximates the set desired fluid balance as shown in hours three and four of the therapy depicted in FIG. 10.

Figure 11:
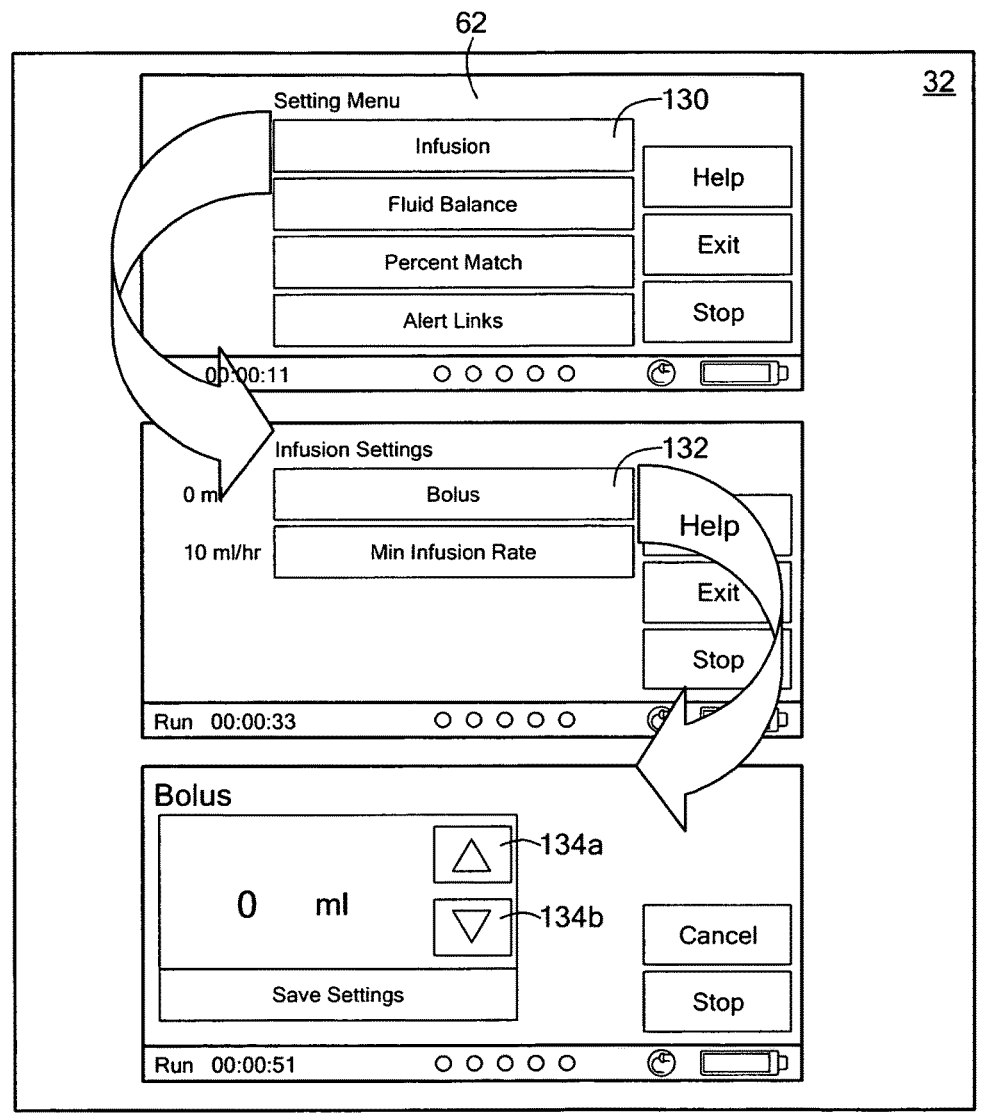
FIG. 11 is a schematic view of the display shown in FIG. 3 configured to allow the user to set a bolus setting.
Figure 12:
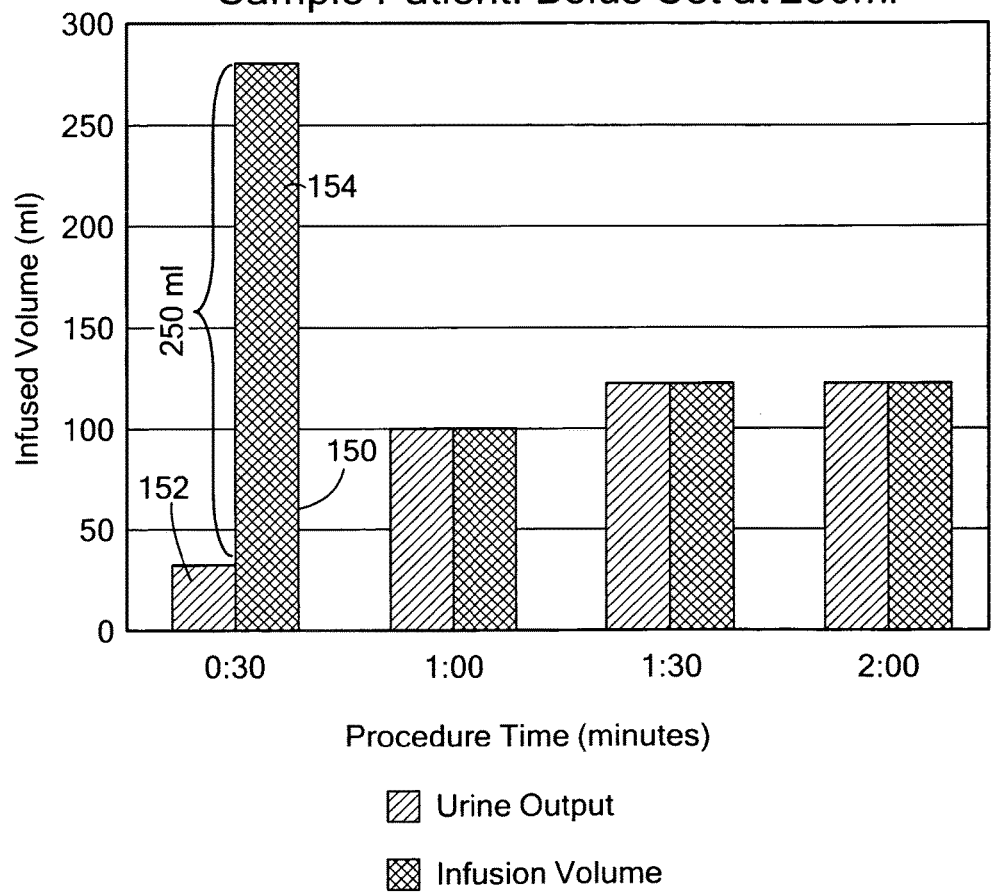
FIG. 12 is a graph showing the results of a patient therapy where a bolus setting has been entered by the user.

FIG. 11 shows how, via touch screen area 62 of touch screen display 32, the user can select infusion settings as shown at 130 which brings up bolus setting 132 which can be adjusted up or down via arrows 134*a* and 134*b*. A bolus may be prescribed by a physician and the invention uniquely allows the nurse to insert a prescribed bolus setting which processing subsystem 20, FIG. 1 automatically delivers by controlling pump 18. In FIG. 12, the bolus has been set by the nurse to 250 ml and in the first 30 minutes of therapy, as shown at 150, the full bolus amount has been delivered to the patient by processing subsystem 20, FIG. 1 controlling pump 18 to deliver a bolus of fluid from fluid source 16. After determining that the patient's urine output was about 25 ml as shown at 152 in FIG. 12, processing subsystem 20, FIG. 1 controls pump 18 to deliver from fluid source 16, 275 mL of fluid as shown at 154. Thereafter, balancing proceeds as shown in FIG. 12. The result is a highly versatile, integrated, easy to use automated system for use in the cath lab or other hospital site to prevent nephropathy, dehydration, over-hydration, and the like.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A device for hydrating a patient, the device comprising:
    a console including:
        a weighing subsystem responsive to a first fluid source and responsive to a urine collection chamber,
        a single pump associated with the console wherein the single pump is configured to pump fluid from the first fluid source directly into the patient to hydrate the patient, and
        a processing subsystem responsive to the weighing subsystem and configured to determine an amount of fluid infused into the patient from the first fluid source and to determine the patient's urine output, based on weight of the urine collection chamber and weight of the first fluid source, the processing subsystem further configured to control the pump to adjust operation of the pump based on the patient's urine output and the amount of fluid infused into the patient from the first fluid source; and
    a user interface in the console including:
        means for setting a desired fluid balance for the patient, and
        means for manually setting an amount of at least one additional fluid delivered to the patient; the processing subsystem being responsive to the set desired fluid balance and the set amount of said at least one additional fluid delivered to the patient;
    the processing subsystem further configured to:
        calculate an actual fluid balance of the patient based on the determined urine output, the determined amount of fluid infused into the patient from the first fluid source, and the set amount of said at least one additional fluid delivered to the patient, and
        further control said pump based on the actual fluid balance and the set desired fluid balance to pump fluid from the first fluid source until the actual fluid balance becomes the same as or approximately the same as the set desired fluid balance.

2. The device of claim 1 in which the user interface includes a display and the processing subsystem is configured to display the actual fluid balance, the set desired fluid balance, the determined urine output, the determined amount of fluid infused into the patient from the first fluid source, and the set amount of the at least one additional fluid delivered to the patient.

3. The device of claim 1 in which the processing subsystem is further configured to detect when the determined urine output is less than said set desired fluid balance and is configured, in response, to control the pump to infuse a minimum preset amount of fluid from the first fluid source.

4. The device of claim 1 in which the processing subsystem is further configured to detect when the determined urine output is greater than a total of the determined amount of fluid infused into the patient from the first fluid source and the set amount of the at least one additional fluid delivered to the patient and, in response, to control the pump to infuse fluid from the first fluid source until the actual fluid balance equals or approximates the set desired fluid balance.

5. The device of claim 1 further including means for setting an amount of at least one additional fluid expelled by the patient.

6. The device of claim 5 in which the processing subsystem is responsive to the set amount of the at least one additional fluid expelled by the patient and configured to calculate an actual fluid balance based on the determined urine output, the determined amount of fluid infused into the patient from the first fluid source, the set amount of said at least one additional fluid delivered to the patient, and the set amount of the at least one additional fluid expelled by the patient.

7. The device of claim 1 further including means for setting a bolus amount of fluid to be injected into the patient from the first fluid source.

8. The device of claim 7 in which the processing subsystem is further configured to be responsive to the set bolus amount and to control the pump until the actual fluid balance is the same as or approximately the same as the set bolus amount.

9. The device of claim 1 in which the console is an integrated console for coupling to a moveable pole.

10. A device for hydrating a patient, the device comprising:

a console including:

a weighing subsystem responsive to a first fluid source and responsive to a urine collection chamber, a pump associated with the console and configured to only pump fluid from the first fluid source into the patient to hydrate the patient, and a processing subsystem responsive to the weighing subsystem and configured to determine an amount of fluid infused into the patient from the first fluid source and to determine the patient's urine output, based on weight of the urine collection chamber and weight of the first fluid source, the processing subsystem further configured to control the pump to adjust operation of the pump based on the patient's urine output and the amount of fluid infused into the patient from the first fluid source; and a user interface in the console including:

means for setting a desired fluid balance for the patient, and means for manually setting an amount of at least one additional fluid delivered to the patient from a separate source;

the processing subsystem being responsive to the set desired fluid balance and the set amount of said at least one additional fluid delivered to the patient, the processing subsystem also configured to:

calculate an actual fluid balance of the patient based on the determined urine output, the determined amount of fluid infused into the patient from the first fluid source, and the set amount of said at least one additional fluid delivered to the patient, and further control said pump based on the actual fluid balance and the set desired fluid balance to pump fluid from the first fluid source until the actual fluid balance becomes the same as or approximately the same as the set desired fluid balance.

\* \* \* \* \*